United States Patent [19]

Trent et al.

[11] Patent Number: 5,693,464

[45] Date of Patent: Dec. 2, 1997

[54] METHOD FOR GENERATING CHROMOSOME REGION-SPECIFIC PROBES

[75] Inventors: Jeffrey M. Trent; Paul S. Meltzer, both of Ann Arbor, Mich.

[73] Assignee: The Regents of the University of Michigan, Ann Arbor, Mich.

[21] Appl. No.: 238,356

[22] Filed: May 5, 1994

Related U.S. Application Data

[63] Continuation of Ser. No. 821,954, Jan. 16, 1992, abandoned, which is a continuation-in-part of Ser. No. 802,364, Dec. 4, 1991, abandoned.

[51] Int. Cl.⁶ .................... C12Q 1/68; C07H 21/04; C12P 19/34; C12N 15/09
[52] U.S. Cl. .................... 435/6; 435/91.2; 435/172.3; 435/320.1; 536/24.3; 536/24.31; 536/24.33
[58] Field of Search ................... 435/6, 91.2, 172.3, 435/320.1; 536/24.31, 24.33, 24.3

[56] References Cited

FOREIGN PATENT DOCUMENTS

WO 90/08821  8/1990  WIPO .

OTHER PUBLICATIONS

Taylor, C.P. et al., "Visualization of diagnostic tumour chromosome aberrations using fluorescence in–situ hybridization"*Eleventh International Workshop on Human Gene Mapping,* London, England, U.K., Aug. 18–22, 1991, *Cytogenet. Cell. Genet.* 58(1–4), 1 page total.

Guan et al., "Isolation of probes for a region of chromosome 6 deleted in malignant melanoma by chromosome microdessection" *Proceedings of the American Association for Cancer Research,* 82nd Annual Meeting, Houston, Texas (May 15–18, 1991) 32:302 (abstract No. 1795).

Cremer, T. et al., "Detection of chromosome aberrations in metaphase and interphase tumor cells by in situ hybridization using chromosome–region specific library probes." *Hum. Genet.* 80:235–246 (1988).

Bronstein, I. et al., "Rapid and Sensitive Detection of DNA in Southern Blots with Chemiluminescence." *Bio Techniques* 8:310–314 (1990).

Traver, C.N. et al., "Rapid Screening of a Human Genomic Library in Yeast Artificial Chromosomes for Single–Copy Sequences." *PNAS, USA* 86:5898–5902 (1989).

Hadano S. et al., "Laser Microdissection and Single Unique Primer Allow Generation of Regional Chromosome DNA Clones from a Single Human Chromosome." *Genomics* 11:364–373 (1991).

Lichter, P. et al., "Florescence in situ hybridization with Alu and L1 Polymerase Chain Reaction Probes for Rapid Characterization of Human Chromosomes in Hybrid Cell Lines." *PNAS USA* 87:6634–638 (1990).

Hampton et al., "Characterization and mapping of microdissected genomic clones from the adenomatous *polyposis coli* (APC) region" *Genomics* (1991) 11:247–251.

Johnson, "Molecular cloning of DNA from specific chromosomal regions by microdissection and sequence–independent amplification of DNA" *Genomics* (1990) 6:243–251.

Kuo et al., "Detection of aneuploidy involving chromosomes 13, 18, or 21, by fluorescence in situ hybridization (FISH) to interphase and metaphase amniocytes" *Am. J. Hum. Genet.* (1991) 49:112–119.

Kuwano et al., "Detection of deletions and cyrptic translocations in Miller–Dieker syndrome by in situ hybridization" *Am. J. Hum. Genet.* (1991) 49:707–714.

Lengauer et al., "Painting of defined chromosomal regions by in situ suppression hybridization of libraries from laser–microdissected chromosomes" *Cytogenet. Cell. Genet.* (1991) 56:27–30.

Lichter et al., "Delineation of individual human chromosomes in metaphase and interphase cells by in situ suppression hybridization using recombinant DNA libraries" *Hum. Genet.* (1988) 80:224–234.

Pinkel et al., "Fluorescence in situ hybridization with human chromosome–specific libraries: detection of trisomy 21 and translocations of chromosome 4" *Proc. Natl. Acad. Sci. USA* (1988) 85:9138–9142.

Tkachuk et al., "Detection of bcr–abl fusion in chronic myelogenous leukemia by in situ hybridization" *Science* (1990) 250:559–562.

Trautmann et al., "Detection of APC region–specific signals by nonisotopic chromosomal in situ suppression (CISS)–hybridization using a microdissection library as a probe" *Hum. Genet.* (1991) 87:495–497.

Callen et al., "Chromosomal origin of small ring maker chromosomes in man: characterization by molecular genetics" *Am. J. Hum. Genet.* (1991) 48:769–782.

(List continued on next page.)

*Primary Examiner*—Jasemine C. Chambers
*Assistant Examiner*—Scott D. Priebe
*Attorney, Agent, or Firm*—Morrison & Foerster LLP

[57] ABSTRACT

The present invention provides rapid, reproducible procedures for generating chromosome region-specific probes (CRSPs) for diagnostic and research applications. Region-specific probes are provided by direct in vitro enzymatic amplification (PCR) of microdissected chromosomal or hybridized DNA from the chromosomal region of interest, followed by labelling for in situ hybridization to metaphase chromosomes and interphase nuclei. CRSP specificity can be further enhanced using a linker-based strategy, wherein linkered DNA (LDNA) sequences prepared from DNA libraries are hybridized to chromosomal DNA in situ, microdissected from the chromosomal region of interest and then directly amplified using the linker as primer. These procedures make it possible to generate a vast number of chromosome region-specific probes without microchemical manipulation after dissection and provide means for identifying cryptic chromosomal alterations previously not amenable to routine cytogenetic analysis. Probes generated by the methods of the present invention can also be used for screening any DNA library of interest.

38 Claims, 3 Drawing Sheets

OTHER PUBLICATIONS

Meese et al., "Development and utilization of a somatic cell hybrid mapping panel to assign NotI linking probes to the long arm of human chromosome 6" *Genomics* (1992) 12:542–548.

Fearon et al., "A genetic model for colorectal tumorigenesis" *Cell* (1990) 61:759–767.

Millikin et al., "Loss of heterozygosity for loci on the long arm of chromosome 6 in human malignant melanoma" *Cancer Res.* (1991) 51:5449–5453.

Mitelman et al., "Report of the committe on chromosome changes in neoplasia" *Cytogenet. Cell. Genet.* (1991)00:000–000. A pre–print copy was previously submitted.

Nowell et al., "Chromosome translocations and oncogenes in human lymphoid tumors" *Am. J. Clin. Pathol.* (1990) 94:229–237.

Pathak et al., "Involvement of chromosome 6 rearrangements in human malignant melanoma cell lines" *Cytogenet. Cell. Genet.* (1983) 36:573–579.

Rowley, "Molecular cytogenetics: Rosetta Stone for understanding cancer–twenty–ninth G.H.A. Clowes Memorial Award Lecture" *Cancer Res.* (1990) 50:3816–3825.

Trent et al., "Chromosome 6q involvement in human malignant melanoma" *Cancer Genet. & Cytogenet.* (1983) 9:177–180.

Trent et al., "Relation of cytogenetic abnormalities and clinical outcome in metastatic melanoma" *New Eng. J. Med.* (1990) 322:1508–1511.

Trent et al., "Tumorigenicity in human melanoma cell lines controlled by introduction of human chromosome 6" *Science* (1990) 247:568–571.

Fountain et al., "Physical mapping of a translocation breakpoint in neurofibromatosis" *Science* (1989) 244:1085–1087.

Warburton, "De novo balanced chromosome rearrangements and extra marker chromosomes identified at prenatal diagnosis: clinical significance and distribution of breakpoints" *Am. J. Hum. Genet.* (1991) 49:995–1013.

Haluska et al., "Oncogene activation by chromosome translocation in human malignancy" *Ann. Rev. Genet.* (1987) 21:321–345.

Weinberg, "A short guide to oncogenes and tumor–suppressor genes" *J. NIH Res.* (1991) 3:45–47.

Gelehrter et al., eds., *Principles of Medical Genetics* (1990) Williams & Wilkins, Baltimore, Maryland, pp. 156–189.

Hassold, "Chromosome abnormalities in human reproductive wastage" *Trends in Genet.* (Apr. 1986) pp. 105–110.

Wesley et al., "Cloning regions of the Drosophila genome by microdissection of polytene chromosome DNA and PCR with nonspecific primer" *Nucleic Acids Res.* (1989) 18:599–603.

Cotter et al., "Gene mapping by microdissection and enzymatic amplification: heterogeneity in leukaemia associated breakpoints on chromosome 11" *Genes, Chromosomes & Cancer* (1991) 3:8–15.

Han et al., "Direct amplification of a single dissected chromosomal segment by polymerase chain reaction: a human sodium channel gene is on chromosome 2q22–q23" *Proc. Natl. Acad. Sci. USA* (1991) 88:335–339.

Ricciardi et al., "Purification and mapping of specific mRNAs by hybridization–selection nd cell–free translation" *Proc. Natl. Acad. Sci. USA* (1979) 76:4927–4931.

Hochgeschwender et al., "Construction and screening of a genomic library specific for mouse chromosome 16" *Proc. Natl. Acad. Sci. USA* (1989) 86:8482–8486.

Senger et al., "Microdissection of banded human chromosomes" *Hum. Genet.* (1990) 84:507–511.

Chehab et al., "Detection of specific DNA sequences by fluorescence amplification: a color complementation assay" *Biochem.* (1989) 86:9178–9182.

Lüdecke et al., "Cloning defined regions of the human genome by microdissection of banded chromosomes and enzymatic amplifications" *Nature* (1989) 338:348–350.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:1:

CCGACTCGAG NNNNNNATGT GG                       22

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:2:

GGATTTGCTG GTGCAGTACA                         20

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:3:

GATCTGTACT GCACCAGCAA ATCC                   24

METHOD FOR GENERATING CHROMOSOME REGION-SPECIFIC PROBES

RELATED APPLICATIONS

This application is a continuation application of U.S. Ser. No. 07/821,954, filed Jan. 16, 1992, now abandoned, which in turn is a continuation-in-part application of U.S. Ser. No. 07/802,364, filed Dec. 4, 1991, abandoned in favor of continuation application U.S. Ser. No. 08/166,280 filed Dec. 13, 1993.

This is a continuation-in-part application of U.S. application Ser. No. 802,364, entitled "Method for Generating Chromosome Region-Specific Probes" filed Dec. 4, 1991, by Trent et al.

SPONSORSHIP

Research related to the present invention was supported in part by the National Institutes of Health PHHS grants CA-29476 and CA-41183. The government may have certain rights to this invention.

FIELD OF THE INVENTION

The present invention relates generally to chromosome region-specific probes (CRSPs) and their preparation and use. More specifically the present invention relates to a rapid, reproducible method of generating chromosome region-specific probes through direct amplification of microdissected chromosomal DNA and DNA hybridized thereto, the probes generated thereby and methods of their use.

BACKGROUND OF THE INVENTION

The identification and analysis of chromosome abnormalities is of great clinical and research importance. Chromosome abnormalities are a significant cause of congenital malformation and are responsible for at least half of spontaneous abortions or miscarriages. Hassold, T., *Trends Genet.* 2:105 (1986); deGrouchy, J. et al., *Clinical Atlas of Human Chromosomes* (John Wiley & Sons, New York, 2d ed, 1984); Gardner, R. et al., *Chromosome Abnormalities and Genetic Counseling* (Oxford Univ. Press, New York, 1989); Gelehrter, T. et al. *Principals of Medical Genetics* (Williams & Wilkins, Baltimore, Md., 1990) pp. 159–189. The analysis of recurring chromosome abnormalities in malignant cells has also become an integral part of the diagnostic and prognostic workup of many human cancers. Heim, S. et al., *Cancer Cytogenetics* (A. Liss, New York, 1987); Sandberg, A., *The Chromosomes in Human Cancer and Leukemia* (Elsevier, New York, 1990); Trent, J. et al., *NEJM* 322:1508 (1990). In addition to these clinical applications, the molecular examination of chromosome abnormalities has facilitated the identification of genes related to the pathogenesis of both hereditary diseases and cancer. Haluska, F. et al., *Ann. Rev. Genet.* 21:321 (1987); Weinberg, R., *J. NIH Res.* 3:45 (1991); Nowell, P. et al., *Am. J. Clin. Pathol.,* 94:229 (1990); Rowley, J., *Cancer Res.* 50:3816 (1990); Fearon, E. et al., *Cell* 61:759 (1990); Fountain, J., *Science* 244:1085 (1989).

Current cytogenetic techniques for chromosome analysis are not, however, entirely satisfactory. One major technical limitation is their inability to unequivocally characterize all cytologically recognizable chromosome rearrangements. For example, amniocentesis may reveal unidentifiable de novo unbalanced translocations or unknown supernumerary marker chromosomes. Warburton, D., *J. Hum. Genet.* 49:995 (1991); Callen, D. et al., *Am J. Hum. Genet.* 48:769 (1991). Likewise, in many human cancers, particularly solid tumors, the presence of unidentifiable marker chromosomes or unidentifiable unbalanced translocations frequently prevents complete karyotypic analysis. Mitelman, F., *Catalog of Chromosome Aberrations in Cancer* (Wiley-Liss, New York,ed. 4th ed, 1991 ); Mitelman, F. et al., *Cytogenet. Cell Genet.* 58:(in press) (1991).

Recently, whole chromosome composite "painting" probes (WCPs) constructed from chromosome-specific DNA libraries have been successfully utilized to visualize specific chromosomes and their derivatives. Pinkel, D. et al., *PNAS* 85:9138 (1988); Lichter, P. et al., *Hum. Genet.* 80:224 (1988); Kuo, W. L. et al., *Am J. Hum. Genet.* 49:112 (1991 ).; Meese, E. et al., *Genomics* (in press) (1991 ). However, identification of unknown chromosomal segments using this approach requires appropriate painting probes for all 24 different human chromosomes. Moreover, this approach yields no regional sublocalization information.

Techniques developed for the generation of chromosome band or region-specific probes have also enjoyed only limited success. In a few instances, structurally altered human chromosomes have been placed in a rodent background (e.g., somatic cell hybrids) to generate probes specific for human material. Although a few segment-specific probes have been generated by this technique, this approach is not very practical in that it requires chromosomal variants immortalized in an appropriate genetic background.

Chromosomal microdissection techniques have also been used to generate band-specific DNA libraries for chromosome painting of dissected regions. For example, fluorescent probes have been prepared from Drosophila and human chromosomes utilizing the polymerase chain reaction (PCR) to amplify the DNA from microdissected chromosome fragments. See Johnson, D., *Genomics* 6: 243 (1990); Trautmann, U. et al., *Hum. Genet.* 87:495 (1991); Lengauer, C. et al., *Cytogenet. Cell Genet.* 56:27 (1991); Hampton, G. et al., *Genomics* 11:247 (1991). These methods use restriction endonuclease digestion and DNA ligation steps to provide the defined sequences flanking the microdissected template DNA for priming of the polymerase chain reaction. These microchemical manipulations of the dissected DNA are labor-intensive, require special equipment, and severely limit the number of probes that can realistically be prepared.

Another approach has been the cloning of locus-specific probes for assessing disease-specific loci such as the Philadelphia chromosome. However, this procedure is limited to those rearrangements for which defined probes are available, which is not the case for the majority of disease-associated chromosome rearrangements. See Tkachuk, D. et al., *Science* 250:559 (1990); Kuwano, A. et al., *Am. J. Hum. Genet.* 49:707 (1991). This approach is also impractical, given the necessity of significant molecular information and appropriate cloned probes for every region of interest (e.g., specific cosmids, YACs, or other large insert clones) to permit evaluation of band-specific abnormalities.

It would thus be desirable to provide a method of generating region-specific probes for any chromosome band or region. It would further be desirable that the method for the preparation of such probes be relatively simple, rapid and reproducible and avoid the painstaking microchemical manipulation of conventional techniques. It would further be desirable to provide a method of generating probes which is not dependent on inordinate amounts of molecular information, reduced chromosome complements or the generation of DNA libraries. It would also be desirable to provide a method wherein a large number of highly specific probes could be easily generated. It would also be desirable that probes generated by this method provide means for identifying all cytologically recognizable chromosomal rearrangements and deletions, including those not amenable to analysis by current cytogenetic techniques. It would further be desirable to provide a method of screening genomic, recombinant or other DNA libraries with a region-specific probe. It would additionally be desirable to provide a method for generating and using probes which is equally applicable to whole chromosomes and specific chromosome regions or bands.

SUMMARY OF THE INVENTION

The present invention comprises a simple rapid method for generating chromosome region-specific probes (CRSPs), the probes generated thereby and their use in clinical and research applications.

The generation of a chromosome region-specific probe (CRSP) generally comprises the microdissection and direct enzymatic amplification of chromosomal or hybridized DNA from the chromosomal region of interest, and labelling of the amplified DNA. Direct amplification is carried out through the polymerase chain reaction (PCR) and in one embodiment is primed by an oligonucleotide primer of random degenerate nucleotides (i.e. universal primer), although Alu or other PCR-based strategies can also be utilized. The present invention thus tremendously simplifies previous microdissection-based procedures by eliminating the need for microchemical processing of the dissected DNA.

In another embodiment of the present invention, linkered DNA (LDNA) carrying a defined oligonucleotide linker is prepared from DNA or cDNA libraries. As used herein, DNA collectively refers to DNA or cDNA except as otherwise indicated. The LDNA, preferably repeat-depleted, is then hybridized in situ to the chromosomal DNA prior to microdissection. Following microdissection of the region of interest, the LDNA of the dissected chromosomal region is directly amplified using the LDNA linker as a primer. This hybrid selective approach provides amplified sequences of great fidelity to the region of interest, resulting in chromosomal region-specific probes of extremely high specificity. Probes prepared by such a scheme of the present invention are also referred to herein as CRSPs, and sometimes as HS (hybridization selected) CRSPs.

CRSPs produced in accordance with the present invention can be used to identify virtually all cytologically recognizable chromosome rearrangements and deletions. Additionally, the methods and probes of the invention provide an avenue for gaining sequence information and can be used to screen genomic or other DNA libraries to assist in gene mapping and isolation. The methods and probes of the present invention now make it possible to generate specific reagents for each chromosome band for band-specific visualization. The present invention further provides for direct selection by hybridization of DNA or cDNA sequences for a given region. In addition, the methods and probes of the present invention can identify cryptic chromosomal alterations which currently are not amenable to routine diagnostic cytogenetic analysis, including unidentifiable supernumerary marker chromosomes, de novo unbalanced translocations of unknown origin and the like. The methods and probes of the invention can also be applied to both normal and abnormal chromosomes and interphase nuclei from any source.

Other features and advantages of the present invention will become apparent from the following description and appended claims, taken in conjunction with the accompanying drawings.

DETAILED DESCRIPTION OF THE PREFERRED EMBODIMENTS

The present invention significantly extends the limits of conventional cytogenetic analysis by providing a rapid source of numerous chromosome band or region-specific probes.

The method of generating chromosome region-specific probes (CRSPs) of the present invention generally comprises the direct PCR amplification of microdissected chromosomal fragments, and labelling of the amplified DNA. By "direct" amplification is meant amplification conducted without microchemical manipulations such as endonuclease digestion and DNA ligation or library generation of the microdissected fragment. By "amplified DNA" is meant the DNA sequence(s) generated or amplified from the microdissected region.

The method of the present invention thus eliminates the need for microchemical techniques and specialized equipment attendant thereto after microdissection. In one embodiment, a DNA oligonucleotide primer is used to directly prime DNA synthesis at intervals along the microdissected DNA template. In this scheme, a "universal" primer of random degenerate nucleotides is preferred, although an Alu or other PCR-based primer strategy can also be utilized. It will also be appreciated that the primer sequence may be altered to increase PCR yield, to enhance signal strength or to facilitate cloning of the PCR product for large scale production.

In another more preferred embodiment, the specificity of CRSPs is enhanced by a linker-primer based strategy which facilitates PCR product recovery. In this embodiment, repeat-depleted linkered DNA (LDNA) sequences are prepared from DNA or cDNA libraries using a defined oligonucleotide linker. The LDNA is then hybridized to chromosomal DNA in situ. Following hybridization, the chromosomal region of interest, with LDNA hybridized thereto, is microdissected and the microdissected LDNA directly amplified using the defined oligonucleotide linker sequence as primer. The resulting LDNA mixture provides chromosome region-specific probes (CRSPs) of extremely high specificity.

Direct enzymatic amplification of the microdissected DNA is carried out by the polymerase chain reaction (PCR) using *Thermus aquaticus* (Taq) polymerase or any other of a number of thermostable enzymes from other sources, such as DNA polymerase from *Thermus flavus, Thermus thermophilus*, and the like. Additionally, one to four cycles of preamplification with a non-thermophilic DNA polymerase such as T7 DNA polymerase or Klenow fragment of *E. coil* DNA polymerase can be carried out before PCR. Reactions are carried out in conventional reaction volumes, using conventional pipetters in 0.5 ml or 1.5 ml microfuge tubes.

The probes of the invention can be labelled using any conventional techniques and labels which provide a detection scheme. Examples of suitable labelling schemes include biotin-avidin immunofluorescence, chromogenic and radioisotopic (e.g. $^3$HTdr) labelling and direct chemical labelling with fluorochromes. Fluorescent biotin-based labels such as biotin-11-dUTP are preferred.

By eliminating the exacting microchemical techniques of prior microdissection-based schemes, probe preparation is dramatically simplified, expedited and accelerated. In addition, because the inherent biochemical inefficiency and losses associated with the microchemical steps are circumvented, the resulting hybridization signal intensities are significantly stronger than those obtained by earlier methods. Probe construction by the methods of the present invention also requires fewer dissected fragments than previous methods, further shortening the procedure. Thus the present method permits the generation of a useful probe within about 24 hours after microdissection.

Probes (CRSPs) generated by the methods of the present invention can be used as whole chromosome or region-specific probes for clinical and research purposes and provide a direct link between cytogenetic and physical mapping techniques. They enable the analysis of any unknown chromosome regions and chromosomal alterations not amenable to analysis by current techniques.

Because of their high degree of chromosomal regional localization, CRSPs of the present invention are also ideally suited for gene isolation procedures, particularly where there is reason to suspect that a given gene is located in a specific chromosome band or region. Although it is possible to clone the PCR products derived from microdissected chromosome, particularly in the case of HS-CRSPs, it may be more advantageous to use this material as a CRSP to screen genomic or other libraries. For example, some PCR products may not clone efficiently, but will still label well as probes. Moreover, the microdissection PCR product falls in the 100–1000 bp range and is a relatively weak hybridization probe when used on a clonal basis. In contrast, two or more CRSPs may fall in the same large insert clone, increasing the intensity of the hybridization signal. It will also be appreciated that the method and probes of the present invention can be employed in any number of schemes for obtaining sequence, location and mapping information. For example, a cosmid contig map can be constructed by screening an appropriate cosmid library with CRSPs of the present invention.

The method and probes of the present invention can be applied to both normal and abnormal metaphase or condensed (e.g. PCC) chromosomes or interphase nuclei from any source (e.g. continuous cell lines, amniocytes, bone marrow or tumor biopsies). In contrast, human probes previously obtained through microdissection were applied only to normal metaphase chromosomes prepared from peripheral blood lymphocytes.

SPECIFIC EXAMPLES

I. CRSP Generation and Methods

Microdissection. Cells in metaphase were harvested for microdissection as previously described by J. Trent & F. Thompson, in Methods in Enzymology, ed. M. Gottesman, (Academic Press, San Diego Calif., 1987) pp. 267–279. Tumor cells were cultured for 48 hours and harvested as therein described. Metaphase spreads were prepared on 24×60 mm #1½ coverslips and stained by trypsin-Giemsa banding. Microdissection was performed with glass microneedles controlled by a Narashige micromanipulator (Model MO-302) attached to an inverted microscope. Prior to use, microneedles were treated with UV light for 5 min (Stratalinker, Stratagene). The dissected chromosome fragment adherent to the microneedle was transferred to a 20 µl collecting drop (containing proteinase K 50 µg/ml) in a 0.5 ml microcentrifuge tube. A fresh microneedle was used for each fragment dissected. After the desired number of copies (25–50) were dissected, the collecting drop was incubated at 37° C. for 1 hr and then at 90° C. for 10 min.

PCR Amplification. The components of the PCR reaction were added to a final volume of 50 µl in the same tube (1.5 µM universal primer— CCGACTCGAGNNNNNNATGTGG-SEQ ID 1 from H. Telenius et al., Abst #27105 Human Gene Mapping Workshop 11, Aug. 16–23, 1991, London, England: 200 µM each dNTP, 2 mM MgCl$_2$, 50 mM KCl, 10 mM TrisHCl pH 8.4, 0.1 mg/ml gelatin; and 2.5 U Taq (*Thermus aquaticus*) DNA polymerase from Perkin-Elmer Cetus). Although a universal primer of random nucleotides and Taq polymerase are utilized in the amplification examples described herein, it will be appreciated that, as described above, alternate primer schemes and other thermostable enzymes suitable for PCR can be used. For example, Alu primer has been successfully utilized in probe preparation in accordance with the principles of the present invention.

The reaction was overlayed with oil and heated to 93° C. for 4 min, then cycled for 8 cycles at 94° C. for 1 min, 1 min at 30° C., and 3 min at 72° C., followed by 28 cycles of 1 min at 94° C., 1 min at 56° C. and 3 min at 72° C., with a 10 min final extension at 72° C. A blank reaction consisting of an identically processed empty collection drop was included with each experiment as a control. The experiment was ordinarily continued only if no DNA synthesis was apparent in the blank reaction as determined by ethidium bromide staining of an agarose gel of the PCR products.

Labelling. To label the CRSP, 2 µl of the microdissection PCR reaction was labelled in a secondary PCR reaction identical to the first except for reduction of the TTP concentration to 100 µM and the inclusion of 100 µM biotin-11-dUTP cycled for 8 cycles of 1 min at 94° C., 1 min at 56° C. and 3 min at 72° C., with a 10 min final extension at 72° C. The products of this reaction were then purified with a Centricon 30 filter and used for in situ hybridization as described below. It will also be appreciated that an equally effective alternative for probe labelling is biotinylation with biotin-11-dUTP in a nick translation reaction. Other suitable labelling schemes can also be employed as previously described.

Hybridization. Hybridization of CRSPs prepared according to the methods described above followed standard Imagenetics (Naperville, Ill.) protocol based on D. Pinkel, et al., *PNAS* 85:9138 (1988). For hybridizations including fluorochrome labelled WCPs (Imagenetics), 10 ng/μl WCP was included in the hybridization. In some experiments, to allow precise localization of the region-specific probe signal with respect to chromosome bands, slides were first processed by trypsin-Giemsa banding, photographed, and then destained by sequential washing in 70% ethanol (1 min), 85% ethanol (1 min), Carnoy's fixative (10 min), 3.7% formaldehyde in PBS (10 min) and PBS (5 min twice) prior to hybridization. Slides were examined with a Zeiss Axiophot microscope equipped with a dual bandpass fluorescein-rhodamine filter.

II. Examples of Applications of CRSP

In Situ Hybridization to Metaphase Chromosomes and Interphase Nuclei. FIG. 1 depicts the method of the present invention including an illustration of chromosome microdissection and the resulting hybridization of the dissected CRSP DNA back to normal lymphocyte metaphase chromosomes (FIG. 1(*i*)). Also illustrated is an example of the hybridization signal obtained from interphase nuclei. More specifically, FIGS. 1(*a*)–(*d*) depicts sequential photographs illustrating the microdissection of chromosome band region 6q21-23. FIGS. 1(*e*)–(*h*) shows a series of dissected chromosomes 6 to illustrate the reproducibility of the dissection. In FIG. 1(*i*), a CRSP for 6q21-23 was hybridized to a normal peripheral blood lymphocyte metaphase chromosome, illustrating the band-specific fluorescence. The inset of FIG. 1(*a*) illustrates hybridization to the domains of interphase nuclei which encompass chromosome 6q21-23.

Identification of Chromosomal Rearrangement. FIG. 2, described in detail below, illustrates the use of a CRSP of the invention to positively identify chromosomal rearrangements which were impossible to identify by standard cytogenetic analysis. A malignant melanoma cell line (UACC-383) was determined by G-banding to contain an unidentifiable de novo translocation [t(6;?)(q14;?)]. A CRSP for the unknown chromosomal material in the translocation chromosome was generated and hybridized back to normal lymphocyte chromosomes. The results clearly indicated that the dissected material was derived from the terminal long arm of chromosome 21(q21→qter). When the CRSP was hybridized back to UACC-383 tumor chromosomes to demonstrate the specificity of the probe, a second previously unrecognized translocation involving chromosome 21, this time with chromosome 1 q was visualized. The derived chromosome 1 in this tumor which displayed the unrecognized translocation with 21 also had an inversion in the long arm with breakpoints at q32 and q44 with the resulting translocation identified as: der(1)t(1;21)(21qter→21q11::1p22-1q32::1q44→1q32). This example demonstrates that the methods and probes of the present invention revealed information previously hidden in the banded karyotype.

FIG. 2(*a*) is a partial metaphase spread of the t(6;?)(q14;?) translocation (arrow). FIGS. 2(*b*)–(*c*) shows the microdissection of the material distal to 6q14 for the generation of a CRSP. FIG. 2(*d*) shows the dissected CRSP hybridized back to tumor metaphase chromosomes: upper row-(left) G-banded normal chromosome 6; (right) normal 6 painted with a FITC-labeled chromosome 6-WCP (Spectrum orange #6 and biotinylated WCP for detection with FITC obtained from Imagenetics); lower row-(left) G-banded unidentifiable translocation chromosome; (center) FITC painting by chromosome 6-WCP illustrating the presence of the short arm and proximal long arm of chromosome 6; (right) simultaneous painting with Spectrum Orange (color not shown) 6-WCP (Spectrum Orange #6 and biotinylated WCP for detection with FITC obtained from Imagenetics), and the CRSP (green - color not shown) identifies the translocation chromosome.

FIG. 2(*e*) shows the hybridization of the CRSP from FIGS. 2(*b*–*c*) to normal lymphocyte metaphase chromosomes: (left) G-banded partial metaphase with arrow to chromosome 21; and (right) the identical cell following hybridization illustrating the dissected material is from chromosome 21 (q21→qter). FIG. 2(*f*) illustrates the CRSP generated in FIG. 2(*c*) hybridized to a normal lymphocyte metaphase documenting probe specificity for human chromosome 21.

Spanning of Translocation Breakpoint. FIG. 3 illustrates two additional applications of the present invention procedure in molecular cytogenetic analysis. In the first, a CRSP was generated for the specific chromosomal band 6q21-22. This probe was hybridized to metaphase cells carrying a reciprocal translocation involving the 6q22 band region [t(6;7)(q22;q21)]. In this experiment, the 6q21-22 probe was applied simultaneously with a chromosome 6-WCP (Spectrum Orange #6 and biotinylated WCP for detection with FITC obtained from Imagenetics), to unequivocally localize the dissected material in this cell. The results, described below, clearly illustrated the application of this approach to span a translocation breakpoint. By selecting two distinct fluorochromes for the CRSP and chromosome 6-WCP, both the normal chromosome 6 and its derivatives could be definitively identified.

Figure 1A:
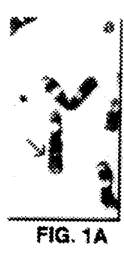
FIGS. 1(a) through (i) illustrates the generation and use of a CRSP according to the principles of the present invention: (a)–(d) are sequential photographs of the microdissection of a chromosome band region; (e)–(h) are photographs of a series of dissected chromosomes 6 which illustrate reproducibility of microdissection; and (i) shows the resulting hybridization of the dissected CRSP back to normal lymphocyte metaphase chromosomes. The inset of FIG. 1(i) illustrates the hybridization signal obtained from interphase nuclei.
Figure 1B:
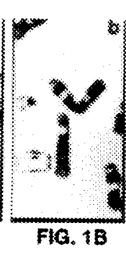
Figure 1C:
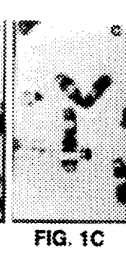
Figure 1D:
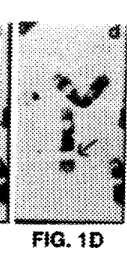
Figure 1E:
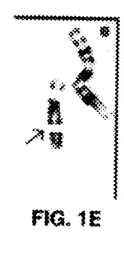
Figure 1F:
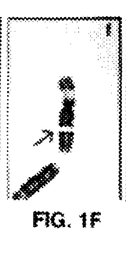
Figure 1G:
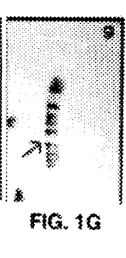
Figure 1H:
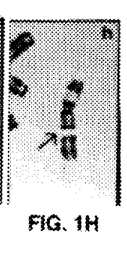
Figure 1I:
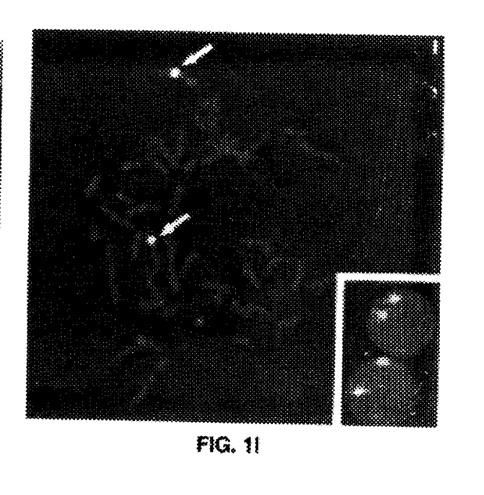
Figure 2A:
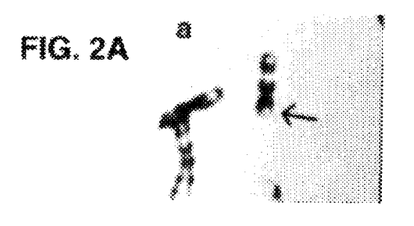
FIGS. 2(a) through (f) illustrates the use of a CRSP according to the principles of the present invention to positively identify chromosomal rearrangements which were impossible to identify by standard cytogenetic analysis.
Figure 2B:
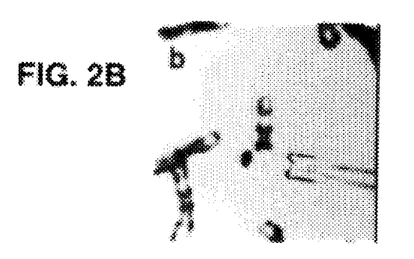
Figure 2C:
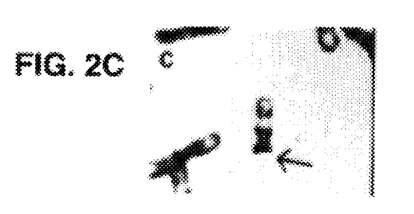
Figure 2D:
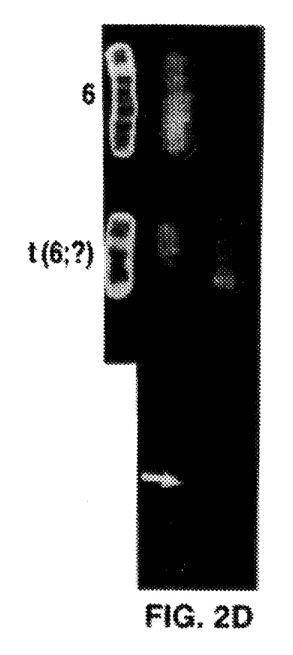
Figure 2E:
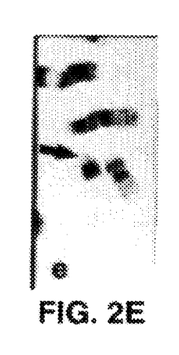
Figure 2F:
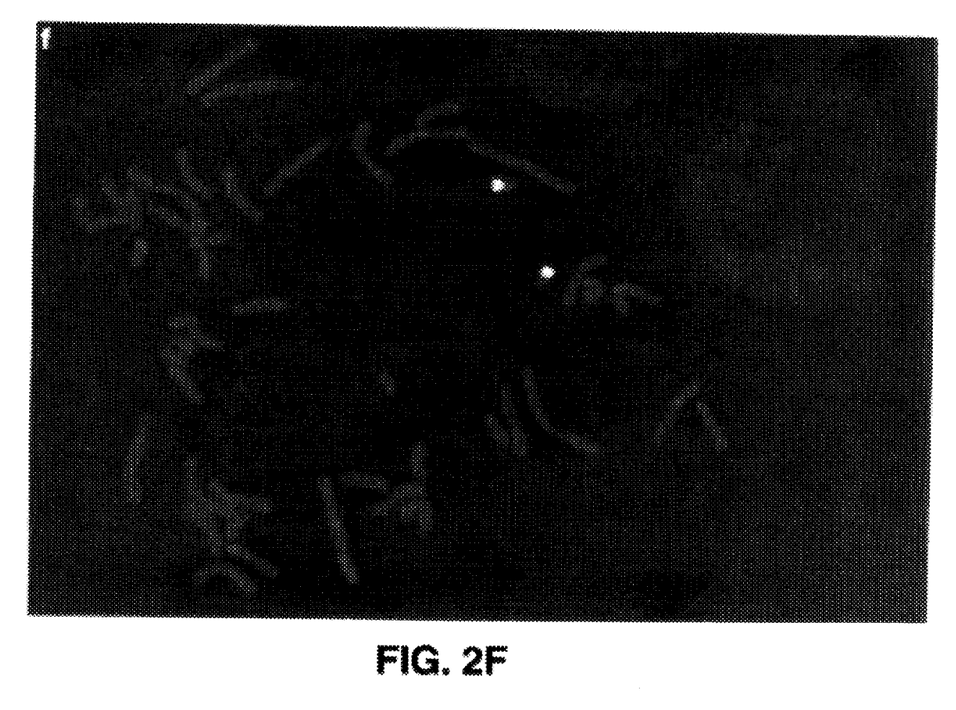
Figure 3A:
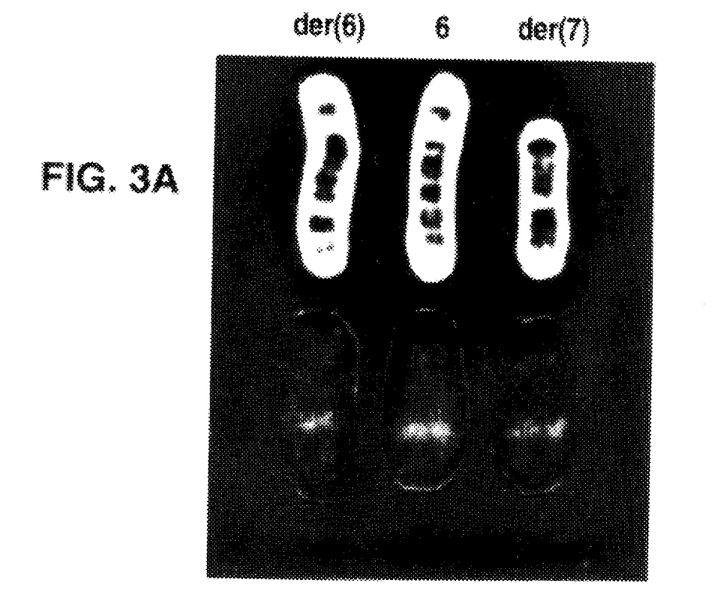
FIGS. 3A through 3C illustrate two applications of the present invention in molecular cytogenetic analysis: (a) the spanning of a translocation breakpoint; and (b)–(c) the assessment of chromosome band-specific loss of heterozygosity (LOH).

FIG. 3(*a*) illustrates the following: upper row-(middle) G-banded normal chromosome 6; (left) derivative (der) chromosome 6; and (right) (der)chromosome 7 present in NIGMS Human Genetic Mutant Cell Repository line #GM05184; lower row-simultaneous hybridization with a chromosome 6-WCP (orange-color not shown) and a CRSP for band 6q21-22 (green-color not shown): (left) der(6) chromosome illustrates the short arm and proximal long arm of chromosome 6 and the yellow band (color not shown) represents the microdissected material spanning the translocation breakpoint; (center) normal chromosome 6 illustrating band location of the probe; (right) der(7) illustrating the distal long arm of chromosome 6 (painted by the chromosome 6-WCP and the 6q21-22 CRSP).

Assessment of Chromosome Band-Specific LOH. The second application of the present invention illustrated in FIG. 3, described below, is the assessment of chromosome band-specific loss of heterozygosity (LOH). In this experiment, chromosomes were obtained directly from a malignant melanoma tumor biopsy. Tumor cells were cultured for 48 hours and harvested as previously described and analyzed by probe hybridization for the possible loss of chromosome 6q21-22 sequences. Loss of sequences from the long arm of chromosome 6 have been implicated in the genesis or progression of malignant melanoma. Trent, J. et al., *Cancer Genet. Cytogenet.* 9:177 (1983); Pathak, S. et al., Cytogenet. Cell Genet. 36:573 (1983); Trent, J. et al., Science 247:568 (1990); Millikin, D. et al., Cancer Res. 51:5449 (1991). Simultaneous hybridization with a chromosome 6-WCP and the 6q21-22 CRSP demonstrated an interstitial deletion in one chromosome 6. LOH was also recognizable in interphase nuclei. These results demonstrate the value of CRSPs for assessing band-specific LOH, thus providing a general approach for identifying deletion of specific chromosome regions in biopsies of human cancers.

Figure 3B:
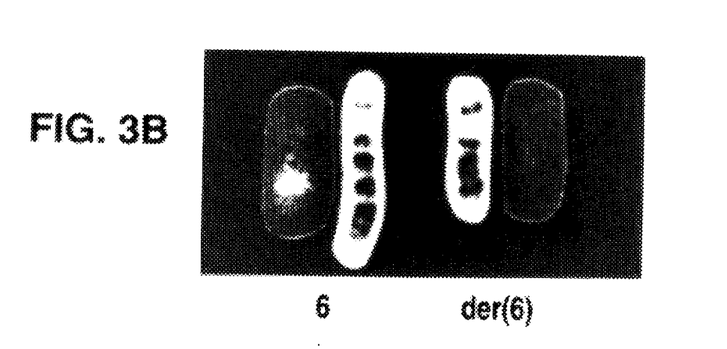
Figure 3C:
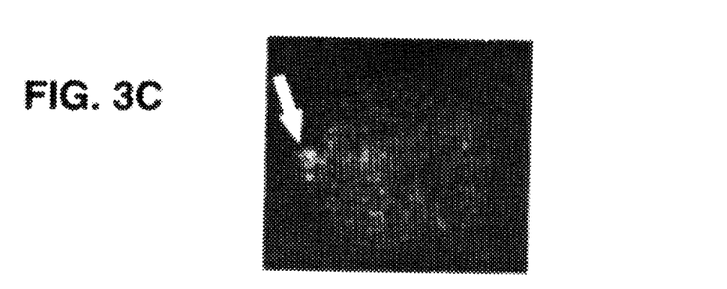

FIG. 3(b) illustrates the use of CRSPs to assess band-specific LOH from the biopsy sample of a melanoma tumor (UM91-023). The center two chromosomes represent a normal chromosome 6 and a chromosome 6 with an interstitial deletion of 6q [del(6)(q15q23)]. Adjacent to each chromosome is an example of the simultaneous use of the chromosome 6-WCP and the 6q21-22 CRSP which documents the loss in the deleted chromosome of sequences recognized by this probe. FIG. 3(c) shows interphase nucleus from the tumor illustrated in FIG. 2(b) documenting the two red domains (color not shown) recognized by the chromosome 6-WCP. Only one chromosome 6 domain (arrow) illustrates hybridization (yellow-color not shown) with the chromosome 6q21-22 CRSPs.

DNA Library Screening for Gene Isolation. A CRSP, generated as described previously, is labelled with a $^{32}$P-nucleotide instead of the chemically modified nucleotide used for in situ hybridization. The resulting radioactive probe is used for hybridization to filters representing any type of genomic or recombinant library which is set up for filter hybridization screening. Such vectors can include plasmids, bacteriophage, cosmids and YACs (yeast artificial chromosomes). An appropriate blocking DNA is used in the hybridization reaction (such as Cot1 DNA, BRL), and the most strongly hybridizing clones are selected as positives. The chromosomal origin of the positives selected in this fashion is confirmed by standard mapping techniques such as fluorescent in situ hybridization or rodent-human somatic cell hybrid mapping.

III. Hybridization Selected CRSPs (HS-CRSPs)

Preparation of linkered DNA. Total human DNA or cDNA (collectively referred to as DNA) is prepared by conventional protocols. Molecular Cloning (2d ed.), J. Sambrook, et al., Cold Spring Harbor Laboratory Press (1989). The DNA is reduced in size to <1000 bp by restriction endonuclease treatment or shearing. An appropriate linker oligonucleotide is added by DNA ligation, which can be either a blunt-ended ligation or sticky-ended ligation. The specific linker is unimportant as long as the sequence is defined for subsequent PCR priming. As an example, total human DNA is digested with MboI, and ligated with a linker consisting of GGATTTGCTGGTGCAGTACA SEQ ID 2 and GATCTG-TACTGCACCAGCAAATCC SEQ ID 3. Johnson, D., Genomics 6:243–251 (1990).

After ligation, the LDNA is purified by Centricon filtration and then depleted of repetitive sequences by hybridization to Cot 1 DNA (BRL) which has been previously biotinylated by nick translation. The repetitive DNA is removed by Streptavidin magnetic beads. The repeat-depleted LDNA is amplified by PCR using the linker primer (GGATTTGCTGGTGCAGTACA) SEQ ID 2 in the example given below.

In Situ Hybridization with Linkered Probe DNA. Cells in metaphase are harvested for microdissection from human tissue cultures (including peripheral blood cultures, continuous cell lines, short term cultures of tumors, body fluids, amniocytes, fibroblasts, lymphocytes and bone marrow) or biopsy samples (including tumor biopsies, bone marrow aspirates, and blood) using conventional cytogenetic techniques. Metaphase spreads are prepared on 24×60 mm #1½ cover slips. Hybridization is based on the standard Imagenetics protocol referred to previously. Cover slips with metaphase spreads of the desired target cell are denatured at 72° C. for 2 min in a bath of 70% formamide 2×standard saline citrate (SSC), dehydrated through an alcohol series and air dried. The cover slip is placed on a slide warmer at 37° C. and 2 µl of hybridization mixture (LDNA, 50% formamide, 10% dextran sulfate, 1×SSC, and 3 µg Cot1 DNA (BRL)) is applied. A cover slip is sealed in place with rubber cement, and the cover slip is incubated overnight at 37° C. in a moist chamber. After hybridization, cover slips are washed three times in 2×SSC/50% formamide at 42° C. for 3 min and then rinsed for 3 min 2×SSC at ambient temperature. The cover slips are then washed in 0.1M sodium phosphate, 0.1% NP-40 pH 8.0 (PN) for 60 min at 45° C.

Chromosome Microdissection and PCR Amplification of Hybridized LDNA. After hybridization, cover slips are Wright stained. Microdissection is performed with glass microneedles controlled by a Narashige micromanipulator (Model MO-302) attached to an inverted microscope. Prior to use, microneedles are treated with UV light for 5 min (Stratalinker, Stratagene). The dissected chromosome fragment adherent to the microneedle is transferred to a 20 µl collecting drop (containing proteinase K 50 µg/ml) in a 0.5 ml microcentrifuge tube. A fresh microneedle was used for each fragment dissected. After the desired number of copies (1–50) are dissected, the collecting drop is incubated at 37° C. for 1 hr and then at 90° C. for 10 min. The components of the PCR reaction are then added to a final volume of 50 µl in the same tube, and PCR is carried out using a single linker oligonucleotide as primer. The resulting PCR product contains a mixture of LDNA sequences which hybridized specifically to the dissected band region, and therefore are highly region-specific CRSPs.

Examples of Utilization of HS-CRSPs. The LDNA PCR product is labelled to provide a CRSP using any suitable means such as biotinylation by nick translation or PCR prior to in situ hybridization. Alternatively, other substituted nucleotides (e.g. digoxygenin or fluorochrome substituted) can be utilized. These can be visualized by standard protocols known to those skilled in the art. The LDNA PCR product can also be labelled with a radioactive nucleotide, and used to screen a recombinant DNA library to isolate large region specific clones or cDNAs. The PCR product can also itself be cloned for large scale production or for the isolation of individual clones which can be used as probes for Southern blot analysis, or library screening. Individual clones can also be sequenced to generate chromosome region specific sequence information which can be used to design primers for PCR in various modes, including screening yeast artificial chromosome (YAC) libraries.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All publications cited herein are incorporated by reference.

We claim:

1. A method for generating a chromosome region-specific DNA of a chromosomal region of interest comprising the steps of:
    (a) providing a library of DNA sequences which includes DNA corresponding to the chromosomal region of interest;
    (b) linking a defined oligonucleotide sequence to at least a portion of each DNA sequence of the library of step (a) to provide linkered DNA (LDNA);
    (c) hybridizing the LDNA of step (b) to chromosomal DNA in situ;
    (d) microdissecting the chromosomal region of interest, the region comprising the hybridized LDNA from step (c) to generate microdissected LDNA; and
    (e) directly amplifying the microdissected LDNA using the defined oligonucleotide sequence as a primer, thereby generating the chromosome region-specific DNA.

2. The method of claim 1, wherein amplification is by a polymerase chain reaction (PCR).

3. The method of claim 1, wherein the linkered DNA is repeat-depleted prior to hybridization.

4. The method of claim 1, wherein the defined oligonucleotide sequence comprises at least one of the following sequences of nucleotides: GGATTTGCTGGTGCAGTACA (SEQ ID NO:2) and GATCTGTACTGCACCAGCAAATCC (SEQ ID NO:3).

5. The method of claim 1, wherein the library of DNA of step (a) is a cDNA library or a genomic library.

6. Chromosome region specific DNA produced by the method of claim 1, and comprised of a mixture of cDNA sequences.

7. The method of claim 1, wherein the chromosomal region of interest is in its normal chromosomal location.

8. The method of claim 1, wherein the chromosomal region of interest is translocated from its normal chromosomal location.

9. The method of claim 1, further comprising the step of:
    (f) cloning the chromosome-region specific DNA, to produce a clone.

10. A library of clones produced by the method of claim 9.

11. A method of locating a chromosomal region of interest in a chromosome sample comprising the steps of:
    (a) providing a chromosome region-specific probe generated by:
        (i) providing a library of DNA sequences which includes DNA corresponding to the chromosomal region of interest;
        (ii) linking a defined oligonucleotide sequence to at least a portion of each DNA sequence of the library of step (i) to provide linkered DNA (LDNA);

(iii) hybridizing the LDNA of step (ii) to chromosomal DNA in situ to generate hybridized LDNA;

(iv) microdissecting the chromosomal region of interest, the region comprising hybridized LDNA from step (iii) to generate microdissected LDNA;

(v) directly amplifying the microdissected LDNA of step (iv) using the defined oligonucleotide sequence as a primer to generate amplified LDNA; and (vi) labelling the amplified LDNA of step (v) to provide the probe; and (b) contacting the chromosome sample with the probe under conditions favorable for hybridization between the probe and complementary nucleic acid sequences in the sample; and (c) detecting hybridization of the probe in the chromosome sample, thereby locating the chromosomal region of interest in the chromosome sample.

12. The method of claim 11, wherein amplification is by a polymerase chain reaction.

13. The method of claim 11, wherein the amplified LDNA provided by step (a)(v) is labeled with a fluorescent or biotin-based label in step (a)(vi).

14. The method of claim 11, wherein the chromosome sample of step (b) is a sample selected from the group consisting of a normal chromosome, an abnormal chromosome, and a chromosome obtained from a biopsy.

15. The method of claim 11, wherein the linkered DNA is repeat-depleted prior to hybridization.

16. The method of claim 11, wherein the defined oligonucleotide sequence comprises at least one of the following sequences of nucleotides: GGATTTGCTGGTGCAGTACA (SEQ ID NO. 2) and GATCTGTACTGCACCAG-CAAATCC (SEQ ID NO. 3).

17. The method of claim 11, wherein the library of DNA of step (a) is a cDNA library or a genomic library.

18. The method of claim 11, wherein the chromosomal region of interest is in its normal chromosomal location.

19. The method of claim 11 wherein the chromosomal region of interest is translocated from its normal chromosomal location.

20. A method of screening a library of DNA clones for clones of a chromosomal region of interest comprising the steps of:

(a) providing a chromosome region-specific probe generated by:

(i) providing a library of DNA sequences which includes DNA corresponding to the chromosomal region of interest;

(ii) linking a defined oligonucleotide sequence to at least a portion of each DNA sequence of the library of step (i) to provide linkered DNA (LDNA);

(iii) hybridizing, in situ, the LDNA of step (ii) to chromosomal DNA containing the region of interest;

(iv) microdissecting the chromosomal region of interest, the region comprising hybridized LDNA from step (iii), to generate microdissected LDNA;

(v) directly amplifying the microdissected LDNA of step (iv) using the defined oligonucleotide sequence as a primer to generate amplified LDNA; and (vi) labelling the amplified LDNA of step (v) to provide the probe;

(b) contacting each clone of the library with the probe under conditions favorable for nucleic acid hybridization; and (c) determining whether and for which clone hybridization has occurred thereby screening the library of DNA clones.

21. The method of claim 20, wherein the library of clones comprises a recombinant DNA library.

22. The method of claim 20, wherein amplification is by a polymerase chain reaction (PCR).

23. The method of claim 20, wherein the amplified LDNA provided by step (a)(v) is labeled with a fluorescent or biotin-based label in step (a)(vi).

24. The method of claim 20, wherein the tinkered DNA is repeat-depleted prior to hybridization.

25. The method of claim 20, wherein the defined oligonucleotide sequence comprises at least one of the following sequences of nucleotides: GGATTTGCTGGTGCAGTACA (SEQ ID NO. 2) and (GATCTGTACTGCACCAGCAAATCC) SEQ ID NO. 3.

26. The method of claim 20, wherein the wherein the library of DNA of step (a) is a cDNA library or a genomic library.

27. The method of claim 20, wherein the chromosomal region of interest is in its normal chromosomal location.

28. The method of claim 20, wherein the chromosomal region of interest is translocated from its normal chromosomal location.

29. A method for generating a chromosome region-specific DNA probe for a chromosomal region of interest comprising the steps of:

(a) providing a library of DNA sequences which includes DNA corresponding to the chromosomal region of interest;

(b) linking a defined oligonucleotide sequence to at least a portion of each DNA sequence of the library of step (a) to provide linkered DNA (LDNA);

(c) hybridizing the LDNA of step (b) to chromosomal DNA in situ;

(d) microdissecting the chromosomal region of interest, the region comprising the hybridized LDNA from step (c), to generate microdissected LDNA; and (e) directly amplifying the microdissected LDNA of step (d) using the defined oligonucleotide sequence as a primer to generate amplified LDNA;

(f) labeling the amplified DNA with a label, thereby generating the chromosome region-specific DNA probe.

30. The method of claim 29, wherein amplification is by a polymerase chain reaction (PCR).

31. The method of claim 29, wherein the linkered DNA is repeat-depleted prior to hybridization.

32. The method of claim 29, wherein the defined oligonucleotide sequence comprises at least one of the following sequences of nucleotides: GGATTTGCTGGTGCAGTACA (SEQ ID NO. 2) and GATCTGTACTGCACCAG-CAAATCC (SEQ ID NO. 3).

33. The method of claim 29, wherein the library of DNA of step (a) is a cDNA library or a genomic library.

34. The method of claim 29, wherein the chromosomal region of interest is in its normal chromosomal location.

35. The method of claim 29, wherein the chromosomal region of interest is translocated from its normal chromosomal location.

36. The method of claim 29, wherein the amplified LDNA provided by step (e) is labeled with a fluorescent or biotin-based label in step (f).

37. A nucleic acid probe produced by the method of claim 29, and comprised of a mixture of cDNA sequences.

38. A nucleic acid probe produced by the method of claim 36, and comprised of a mixture of cDNA sequences.

* * * * *

UNITED STATES PATENT AND TRADEMARK OFFICE
CERTIFICATE OF CORRECTION

PATENT NO. : 5,693,464

DATED : December 2, 1997

INVENTOR(S) : Jeffrey M. Trent and Paul S. Meltzer

It is certified that error appears in the above-identified patent and that said Letters Patent is hereby corrected as shown below:

On the title page, item [56]
In the References Cited, Other Publications, in the publication to Guan et al., "microdes" should be --microdis-- in the publication to Callen et al., "maker" should be --marker-- in the publication to Han et al., after the word "human" insert --brain-- in the publication to Ricciardi et al., "nd" should be --and--

Column 6, line 31, "27105" should be --27106--
line 34, "U Taq" should be --U taq--
line 36, "Taq" should be --taq--

Column 7, line 50, "1 q" should be --1q--

Column 9, line 57, "Centricon" should be --centricon--

Column 10, line 9, "2xstandard" should be --2x standard--
line 13, "1xSSC" should be --1x SSC--
line 18, "2xSSC" should be --2x SSC--
line 30, "µg" should be --µl--

Column 12, line 45, "region specific" should be --region-specific--

UNITED STATES PATENT AND TRADEMARK OFFICE
CERTIFICATE OF CORRECTION

PATENT NO. : 5,693,464

DATED : December 2, 1997

INVENTOR(S) : Jeffrey M. Trent and Paul S. Meltzer

It is certified that error appears in the above-identified patent and that said Letters Patent is hereby corrected as shown below:

line 46, "cDNA" should be --LDNA--

Column 13, line 13, "nucleic acid" should be --DNA--
    line 19, after "reaction" insert --(PCR)--
    line 65, "clone" should be --clones--

Column 14, line 8, "tinkered" should be --linkered--
    line 14, delete "("
    line 14, ") SEQ ID NO. 3" should be -- (SEQ ID NO.3)--
    line 15, delete "the wherein"
    line 63, "cDNA" should be --LDNA--
    line 65, "cDNA" should be --LDNA--

Signed and Sealed this

Thirty-first Day of March, 1998

Attest:

BRUCE LEHMAN

Attesting Officer      Commissioner of Patents and Trademarks